US007135040B2

(12) United States Patent
Wang et al.

(10) Patent No.: US 7,135,040 B2
(45) Date of Patent: Nov. 14, 2006

(54) MEDICAL GUIDE TUBES

(75) Inventors: Shu Wang, Singapore (SG); Seeram Ramakrishna, Singapore (SG); Bini Thumbarathy Balakrishnan, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 160 days.

(21) Appl. No.: 10/328,930

(22) Filed: Dec. 23, 2002

(65) Prior Publication Data

US 2004/0122454 A1 Jun. 24, 2004

(51) Int. Cl.
*A61F 2/06* (2006.01)
(52) U.S. Cl. .................... 623/1.51; 623/1.15; 623/1.52
(58) Field of Classification Search ............. 623/23.64, 623/23.71, 11.11
See application file for complete search history.

(56) References Cited

U.S. PATENT DOCUMENTS

| 4,870,966 | A |  | 10/1989 | Dellon et al. ............... 128/334 |
|---|---|---|---|---|
| 5,019,087 | A |  | 5/1991 | Nichols ...................... 606/152 |
| 5,026,381 | A |  | 6/1991 | Li ............................. 606/152 |
| 5,147,399 | A | * | 9/1992 | Dellon et al. ............... 606/152 |
| 5,656,605 | A |  | 8/1997 | Hansson et al. .............. 514/21 |
| 5,925,053 | A |  | 7/1999 | Hadlock et al. ............ 606/152 |
| 6,090,117 | A |  | 7/2000 | Shimizu ..................... 606/152 |
| 6,095,148 | A | * | 8/2000 | Shastri et al. ............... 128/898 |
| 6,596,296 | B1 | * | 7/2003 | Nelson et al. .............. 424/426 |

FOREIGN PATENT DOCUMENTS

EP          0 652 778 B1       3/2000

OTHER PUBLICATIONS

Paul Weiss, "The Technology of Nerve Regeneration: a review, Sutureless Tubulation and Related Methods of Nerve Repair", Aug. 2, 1944, *J. Neurosurg.*, 1944, I, pp. 400-450.
M.F. Meek et al., "Evaluation of functional nerve recovery after reconstruction with a new biodegradable poly (DL-lactide-ε-caprolactone) nerve guide", *International Journal of Artificial Organs*; 1997, vol. 20, No. 8, pp. 463-468.
M.F. Meek et al, "Evaluation Functional Nerve Recovery . . . Reconstruction with a Poly (DL-Lactide-ε-Caprolactone) Nerve Guide Filled with Modified Denatured Muscle Tissue", *Microsurgery*, 1996, 17(10), pp. 555-561.
W.F.A. den Dunnen et al., "Light-microscopic and electron-microscopic evaluation of short-term nerve regeneration using a biodegradable poly (DL-lactide-ε-caprolactone) nerve guide", *Journal of Biomedical Materials Research*, vol. 31, pp. 105-115 (1996).
W.F.A. den Dunnen et al., "A new PLLA/PCL copolymer for nerve regeneration", *Journal of Materials Science: Materials in Medicine*, 4 (1993) pp. 521-525.

(Continued)

*Primary Examiner*—Corrine McDermott
*Assistant Examiner*—Christopher Prone
(74) *Attorney, Agent, or Firm*—Barnes & Thornburg LLP

(57) ABSTRACT

Polymeric fibers were microbraided around a mandrel to make a tubular guide tube for nerve regeneration. The polymer used for the fibers was one of poly(L-lactide-co-glycolide) (10:90 PLGA) and chitosan. These polymers are biodegradable and biocompatible. The tubes were studied for their surface morphology and swelling behavior. Biological performance of the tubes was examined in the rat sciatic nerve model with a 12 mm gap. One month after implantation nine out of ten rats showed successful nerve regeneration. Morphometric analysis of regenerated nerves confirmed the quality of the regeneration compatible with those offered by other types of biodegradable nerve guide tubes. The tubes were flexible, permeable and showed no swelling.

18 Claims, 3 Drawing Sheets

OTHER PUBLICATIONS

Robert D. Keeley et al., "The Artificial Nerve Graft: A Comparison of Blended Elastomer-Hydrogel with Polyglycolic Acid Conduits", *Journal of Reconstructive Microsurgery*, vol. 7, No. 2, Apr. 1991, pp. 93-100.

Tessa Hadlock et al., "A Tissue-Engineered Conduit for Peripheral Nerve Repair", *Arch. Otolaryngol Head Neck Surg.*, vol. 124, Oct. 1998, pp. 1081-1086.

Tessa Hadlock et al., "A Polymer Foam Conduit Seeded with Schwann Cells Promotes Guided Peripheral Nerve Regeneration", *Tissue Engineering*, vol. 6, No. 2, 2000, pp. 119-127.

Chung-Bu Jenq et al., "Nerve Regeneration Changes with Filters of Different Pore Size", *Experimental Neurology* 97 (1987), pp. 662-671.

W.F.A. den Dunnen et al., "Biological performance of a degradable poly (lactic acid-ε-caprolactone) nerve guide: Influence of tube dimensions", *Journal of Biomedical Materials Research*, vol. 29 (1995), pp. 757-766.

Israel Engelberg et al., "Physico-mechanical properties of degradable polymers used in medical applications: a comparative study", *Biomaterials* 1991, vol. 12 Apr., pp. 292-304.

R.F. Valentini et al., "Polymer electret guidance channels enhance peripheral nerve regeneration in mice", *Brian Research*, 480 (1989), pp. 300-304.

G. Lundborg et al., "A new Type of 'bioartificial' Nerve Graft for Bridging Extended Defects in Nerves", *Journal of Hand Surgery*, (British and European vol., 1997) 22B, pp. 299-303.

B.R. Seckel et al., "Hyaluronic Acid Through a New Injectable Nerve Guide Delivery System Enhances Peripheral Nerve Regeneration in the Rat", *Journal of Neuroscience Research*, 40 (1995), pp. 318-324.

Karl Hekimian et al., "Continuous Alteration of the Internal Milieu of a Nerve-Guide Chamber Using an Osmotic Pump and Internal Exhaust System", *Journal of Reconstructive Microsurgery*, vol. 11, No. 2 Mar. 1995, pp. 93-98.

E.J. Furnish et al., "Tissue Engineering of the Peripheral Nervous System", *Frontiers in Tissue Engineering, Elsevier Science*, 1998, pp. 512-535.

Michael J. Lysaght et al., "An Economic Survey of the Emerging Tissue Engineering Industry", *Tissue Engineering*, vol. 4, No. 3, 1998, pp. 231-238.

Carole A. Heath et al., "The development of bioartificial nerve grafts for peripheral-nerve regeneration", *Trends Biotechnol.*, Apr. 1998, Vo.16, pp. 163-168.

Moriaki Suematsu, "Tubulation for Peripheral Nerve Gap: Its History and Possibility", *Microsurgery*, 10 (1989), pp. 71-74.

A.M. Reed et al., "Biodegradable polymers for use in surgery poly (glycolic)/poly (lactic acid) homo and copolymers: 2. *In vitro* degradation", *Polymer*, 1981, vol. 22, Apr., pp. 494-498.

James W. Fawcett et al., "Peripheral Nerve Regeneration", *Annu. Rev. Neurosci.*, 1990, 13, pp. 43-60.

Brooke R. Seckel, "Enhancement to Peripheral Nerve Regeneration", *Muscle & Nerve*, Sep. 1990, pp. 785-800.

R. Giardino et al. "Biological and synthetic conduits in peripheral nerve repair: a comparative experimental study", *The International Journal Artificial Organs* vol. 18, No. 4, 1995, pp. 225-230.

Michael Merle et al., "Complications from Silicon-Polymer Intubulation of Nerves", *Microsurgery* 1989, 10(2), pp. 130-133.

Thomas R. Stevenson et al., "Tubular Nerve Guide and Epineurial Repair: Comparision of Technique for Neurorrhaphy", *Journal of Reconstructive Microsurgery*, vol. 10, No. 3, May 1994, pp. 171-174.

Simon J. Archibald et al., "A Collagen-Based Nerve Guide Conduit for Peripheral Nerve Repair: An Electrophysiological Study of Nerve Regeneration in Rodents and Nonhuman Primates", *The Journal of Comparative Neurology*, 306 (1991), pp. 685-696.

Annie Laquerriere et al., "Effect of basic Fibroblast Growth Factor and α-Melanocytic Stimulating Hormone on Nerve Regeneration Through a Collagen Channel", *Microsurgery*, 15(3), 1994, pp. 203-210.

L.J. Chamberlain et al., "Early peripheral nerve in collagen and silicone tube implants: Myofibroblasts and the cellular response", *Biomaterials*, vol. 19 (1998), pp. 1393-1403.

Satoru Yoshii et al., "Peripheral nerve regeneration along collagen filaments", *Brain Research*, 888 (2001), pp. 158-162.

N. Nicoli Aldini et al., "Effectiveness of a bioabsorbable conduit in the repair of peripheral nerves", *Biomaterials*, vol. 17, No. 10, (1996), pp. 959-962.

Kyriacos A. Athanasiou et al., "Sterilization, toxicity, biocompatibility and clinical applications of polylactic acid/polyglycolic acid copolymers", *Biomaterials*, vol. 17, No. 2, pp. 93-102.

M.F. Meek et al., "Electronmicroscopical evaluation of short-term nerve regeneration through a thin-walled biodegradable poly (DLLA-ε-CL) nerve guide filled with modified denatured muscle tissue", *Biomaterials*, vol. 22 (2001), pp. 1177-1185.

M. Foidart-Dessalle et al., "Sciatic Nerve Regeneration through Venous or Nervous Grafts in the Rat", *Experimental Neurology*, vol. 148 (1997), pp. 236-246.

Friederike von Burkersroda et al., "Why degradable polymers undergo surface erosion or bulk erosion", *Biomaterials*, vol. 23 (2002), pp. 4221-4231.

Markus S. Widmer et al., "Manufacture of porous biodegradable polymer conduits by an extrusion process for guided tissue regeneration", *Biomaterials*, vol. 19 (1998), pp. 1945-1955.

Shu Wang et al., A new nerve guide conduit material composed of a biodegradable poly(phosphoester), *Biomaterials*, vol. 22 (2001), pp. 1157-1169.

Andrew C.A. Wan et al., "Fabrication of poly(phosphoester) nerve guides by immersion precipitation and the control of porosity", *Biomaterials*, vol. 22 (2001), pp. 1147-1156.

G. Bechtold et al., "Pultrusion of Micro-Braided GF/PA6 Yarn"—Abstract page, *Advanced Composites Letters on-line Abstracts*, vol. 8, Issue 9, 1999, 1 page.

\* cited by examiner

MEDICAL GUIDE TUBES

BACKGROUND

This invention relates to tubes which are useful as medical devices in a number of medical applications, including nerve re-generation, and to the production of such tubes.

Because mature neurons do not replicate, nerve injuries present a challenge for successful rehabilitation. However, under the right conditions, axon extensions of peripheral nerves can regenerate over gaps caused by injury, reconnecting with the distal stump and eventually re-establishing nerve function. Current treatments for an injury-induced break in a nerve typically rely on donor tissue obtained from a second operative site of the patient. The donor tissue may be an autologous nerve graft, vein graft or arterial graft which is sutured to the two ends of the severed nerve. However, these treatments raise the possibility of function loss at the donor site, formation of potential painful neuromas, and structural differences between donor and recipient grafts, not to mention a potential shortage of graft material where extensive repairs are required. A promising alternative for nerve regeneration which avoids the above problems is an artificial graft.

The artificial graft is a synthetic tube that bridges the gap between the nerve stumps and directs and supports nerve regeneration. The tube, which is known as a nerve guide conduit, or NGC, may be implanted empty, or it may be filled with growth factors, cells or fibers. The supply of NGCs is unlimited, and the tubes can be fabricated to optimum dimensions for nerve regeneration. Therefore, methods of producing suitable NGCs have been of great interest in recent years. NGCs have been produced from various biocompatible materials, such as collagen, PTFE, silicon, polyethylene, PLLA/CL, PGA, PLGA, and poly (phosphoester). Nerve guide conduits fabricated from biodegradable polymers are preferred over non-biodegradable polymers due to the obvious advantage of eliminating a second surgery to remove the NGC. Further, if a non-biodegradable tube is not removed after nerve regeneration, it leads to problems such as chronic tissue response or nerve compression.

Some known NGCs have a rigid structure. A drawback with these is that they may break after implantation. Other known NGCs are not particularly strong and may, for example, rip when being sutured in place or break after implantation. There is therefore a need for an improved NGC which may avoid some of the problems attendant with existing NGCs.

SUMMARY OF INVENTION

An NGC is braided from individual fibers or from fiber bundles. Given the small diameter of the fibers (which may be about 20 microns), the process is referred to as microbraiding. The fibers are biocompatible biodegradable polymerics, such as PLGA and chitosan.

According to the invention, there is provided a method of medical treatment, comprising: implanting a flexible, porous, seamless, biodegradable, biocompatible fibrous tube.

According to another aspect of the present invention, there is provided a method of forming a medical device, comprising: microbraiding biodegradable polymer fibers about a mandrel to form a porous tube.

According to a further aspect of the present invention, there is provided a medical device, comprising: a flexible, porous, seamless, biodegradable, biocompatible fibrous tube which may be filled with a biocompatible medium.

A further aspect of the present invention, comprises use of a flexible, porous, seamless, biodegradable, biocompatible fibrous tube as a medical device.

Other features and advantages of the invention will become apparent from a review of the ensuing description, in conjunction with the drawings.

BRIEF DESCRIPTION OF THE DRAWINGS

In the figures which illustrate example embodiments of the invention.

DETAILED DESCRIPTION

Figure 1:
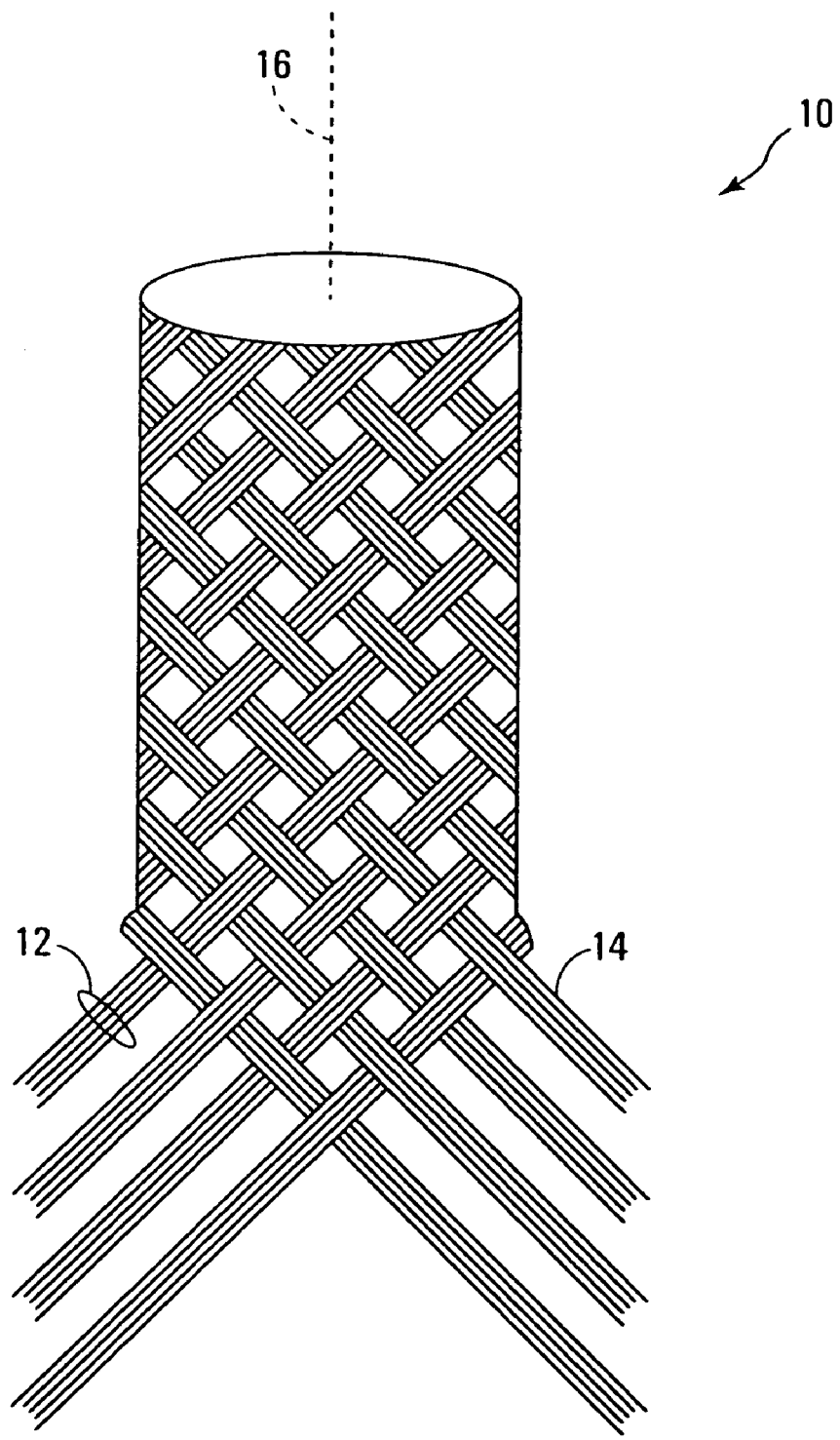
FIG. 1 is a schematic view of a portion of an NGC made in accordance with this invention.

FIG. 1 shows a partially braided NGC 10 made in accordance with this invention. As will be apparent from FIG. 1, the NGC is comprised of braided strands 12 of fibers 14. Each strand may comprise a bundle of fibers and each fiber itself may be a twisted bundle of monofilaments. The monofilaments, and hence the fibers 14, are biocompatible biodegradable polymers. Suitable polymeric fibers are made of 10:90 poly(L-lactide-co-glycolide) (PLGA) or chitosan. The fibers may have a diameter of about twenty microns. The NGC 10 may have an internal diameter of about 1.27 mm, equivalent to the diameter of the axon of a peripheral nerve. The angle made between a strand and the central axis 16 of the tube may be about 45°. Wall thickness of the NGC is a function of fiber thickness (i.e., diameter) and the number of fibers in each fiber bundle. By virtue of being braided, nerve guide conduit 10 has the advantage of being highly flexible and easily suturable to the proximal and distal nerve stumps without tearing. Further NGC 10 has pores resulting from the spaces between crossing fibers which allow the admission of nutrients.

Figure 2:
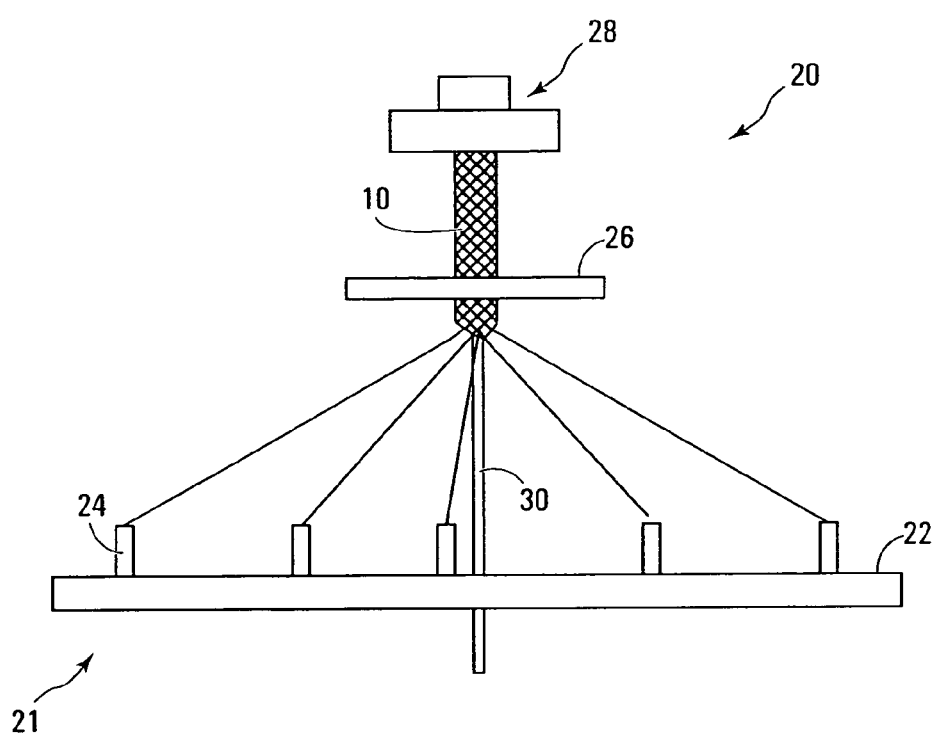
FIG. 2 is a schematic view of apparatus for making the NGC of FIG. 1.

Microbraiding apparatus for manufacturing NGC 10 is illustrated in FIG. 2. Turning to FIG. 2, microbraiding apparatus 20 comprises a microbraider 21 with a track plate 22 supporting spindles 24, a spaced forming plate 26 with a central aperture, and a braid puller 28. Such a microbraider 21 is commercially available from, for example, Kokubun Ltd. of Japan. Microbraiders are normally used in the making of yarns used in the manufacture of fiber reinforced composites for engineering applications. These yarns are not tubular in nature. However, microbraiding apparatus 20 additionally has a cylindrical mandrel 30 which is inserted through the aperture in the forming plate 26 of the microbraider 21. The mandrel may have a surface with a low co-efficient of friction, such as a TEFLON™ surface, and an outer diameter matching the desired interior diameter of the NGC 10 (FIG. 1) as, for example, 1.27 mm.

To braid an NGC, the number of fibers required for each strand is formed into a fiber bundle and wound onto each of the spindles of the microbraiding machine. The ends of the fiber bundles from the spindles are then pulled to the centre of the microbraider 21 and attached to the braid puller 28. The mandrel is inserted through the convergence point 32 and forming point 34 of the microbraider 21 from the bottom and pulled upwards. The machine 12 is then switched on to braid, and a tubular structure of any desired length is obtained. The microbraider is then turned off and NGCs of the required length are cut from the tubular structure while on the mandrel. In this regard, the mandrel may be much longer than an individual NGC in order to facilitate handling. Where the NGC is made of PLGA fibers (which melt when heated), the tubular structure may be cut a heated knife to melt the ends of the fibers so as to prevent the fibers from unravelling. Where the NGC is made of chitosan fibers (which do not melt when heated), the tubular structure is cut and the severed ends dipped in an acetic acid solvent to prevent the fibers from unravelling. The mandrel is then removed. Where the mandrel has a surface with a low co-efficient of friction, it may be removed with less likelihood of damage to the tube.

The porosity of the tubular structure obtained by microbraiding can be varied by changing any of the following parameters, the braiding angle, number of monofilaments in a fibre, number of fibers in a bundle, and the number of fiber bundles.

For example, a suitable PLGA NGC may be obtained by employing 10:90 poly(L-lactide-co-glycolide) fiber composed of ten monofilaments wound together so as to have a diameter of about 20 microns. The PLGA fibers are wound into bundles with six fibers per bundle. The bundles are then wound onto spindles of a microbraider that has ten spindles and the bundles are braided with a braiding angle of 45°. The resulting NGC has ten strands and a wall thickness of about 200 to 300 microns. The size of the pores found between the crossing of the fibers is about 50~100 µm.

Once braided and cut to an appropriate length, the NGC is ready for use. Optionally, during implantation, the lumen of the tube may be filled with saline, or with another biocompatible medium.

The fibrous structure of the tube makes it easy to be sutured to the proximal and distal stumps without tearing. The highly porous structure of the tube makes it highly permeable, which is essential for the entry of nutrients into the tube lumen to promote nerve regeneration and at the same time provides a barrier to prevent the infiltration of unwanted tissues into the tube from outside. The tube also acts as a barrier to prevent sprouting out of axons from inside to outside of the tube. The tube has no problem with tube breakage, which is often encountered with other types of solid-walled polymer tubes.

It is easy to fabricate braided NGC 10 with the present microbraiding technique into any required length and diameter: the tube has no dimensional limitations. Further, it will be apparent that the braided NGC is seamless.

While the braided NGC 10 may be fabricated from PLGA or chitosan, other biodegradable materials may be used, if they are available in fiber form. The method of fabrication does not involve heating or chemical reactions during tube formation. Thus, a material which is not stable in the presence of heat or chemicals and cannot be tubulated by other methods, can be tubulated by the described microbraiding technique, provided only it is in fiber form.

A nerve guide conduit has to finally degrade from its site of implantation after serving its purpose. Poly(L-lactide-co-glycolide) (PLGA) polymer is known to undergo degradation in the physiological environment. PLGA is a copolymer of hydrophobic poly lactic acid (PLA) and hydrophilic poly glycolic acid (PGA). The ratio of PLA and PGA may be 10:90 in the PLGA microbraided NGCs. The mechanism of degradation is by hydrolysis. PLA has a bulky methyl group which resists the attack of water molecules and hence it is hydrophobic and has a slower degradation rate compared to PGA which is easily attacked by water. PGA has no bulky methyl group in its chemical structure and hence it is hydrophilic and undergoes faster degradation. The degradation products are poly lactic acid and poly glycolic acid respectively. PGA is highly crystalline. Crystallinity is rapidly lost in copolymers of glycolic acid and lactic acid. These morphological changes lead to an increase in the rate of hydrolysis. Thus, copolymers tend to degrade more rapidly than PGA or PLA. The presence of 10% PLA in the copolymer PLGA slows down the degradation to a certain extent in the tube. The degradation rate of the PLGA (10:90) tube was found to be optimum for nerve regeneration.

Swelling of the tube is a common feature observed in biodegradable nerve guide conduits. Swelling may be due to water uptake into a porous structure. Also, as the degradation of the tube starts, the polymer is broken down into smaller degradation products which may absorb water and enhance swelling. To test the swelling of the microbraided NGCs 10, weighed microbraided PLGA NGCs were placed in 10 ml of phosphate buffer pH7.4, sealed and incubated at 37° C. At selected points in time, the tubes were removed from the solution, blotted with an absorbent tissue and weighed for weight increase due to water absorption. Four samples were studied at each selected point in time. The percentage weight remaining (W %) was calculated according to the following equation $$W(\%) = (W_f/W_i) \times 100$$

Where, $W_f$ is the weight of swollen tube and $W_i$ is the initial weight of the tube.

In the present study, the PLGA tubes showed no swelling, as there was no increase in weight of the tubes observed. This is advantageous for nerve regeneration, as the lumen space will be maintained constant.

Ten male Wistar rats (200–250 g) were used for an implantation study of microbraided NGCs. For the study, 10:90 PLGA NGCs were used, being fabricated in accordance with the example parameters given above so as to have a wall thickness of 200 to 300 microns and an internal diameter of 1.27 mm. The NGCs were 16 mm long. After anaesthetising with pentobarbital, the right sciatic nerve of the rat was exposed through a 3 cm long skin incision on the thigh and retraction of the gluteus maximus muscle. The nerve was freed from the surrounding tissue and transected at the mid-thigh level, proximal to the tibial and peroneal bifurcation. A 6–8 mm piece of the nerve was removed and then the proximal and distal nerve stumps were pulled 2 mm into each opening of the NGC, leaving a 12 mm interstump gap. The two stumps were fixed within the empty tubes with a single 10-0 perineural suture. Before the proximal stump was pulled into the microbraided NGC, the tube was filled with saline. Eight other rats were studied for autograft repair. The transected nerve was reversed and sutured back between the nerve stumps. The surgery was performed under an Olympus operating microscope. The muscle layers were closed with 4/0 silk sutures and the skin closed with Michel clips.

One month after implantation, the rats were anaesthetised again and the sciatic nerve together with the microbraided NGCs were re-exposed and carefully isolated from the surrounding tissues. The nerve trunk distal to the tube was pinched with a pair of forceps. Contraction of muscle on the back or movement of the leg indicates the presence of regenerating nerve inside the tube. The microbraided PLGA tubes were then excised together with the intubated nerves. The tubes were then removed carefully to isolate the regenerated nerve.

For immunostaining, the regenerated nerves were fixed with 4% paraformaldehyde and 2.5% glutaraldehyde in Phosphate Buffered Saline (PBS) overnight before immunostaining. Twenty-micrometer thick transverse sections were cut on a cryostat and collected onto gelatin-coated glass slides. The sections were stained with mouse monoclonal antibodies against the 68 kDa neurofilament protein.

For morphometric analysis after one month implantation, the regenerated nerve was fixed with 4% paraformaldehyde and 2.5% glutaraldehyde in PBS for three days. It was then post-fixed with 1% osmium tetraoxide for 2 hours at room temperature, and washed with PBS. Then it was dehydrated through an ascending series of ethanol at room temperature. After dehydration it was then infiltrated with a mixture of acetone and resin in the ratio of 1:1 for 30 minutes and 1:6 overnight at room temperature. Then it was subjected to three changes of fresh resin. The first change of fresh resin was for 20 minutes at room temperature and then to 40° C. for 30 minutes. The second change of fresh resin was for 1 hour at 45° C. and the third change of fresh resin was for 1 hour at 50° C. It was then embedded in fresh resin and polymerised at 60° C. for 24 hours. The nerves were cut into cross sections of 1 μm thickness, and stained with toluidine blue. Quantitative evaluation was carried out at the middle of the regenerated nerve cables using Image Tool Analyser,. For each sample, six areas of about 500 μm² from two cross sections and about 200–300 fibers were evaluated.

One week after implantation, the NGC chamber had become filled with a solid structure that bridged the two nerve stumps. The solid structure was present in all the tubes examined and was firmly connected with the stumps. These were fibrin matrices. Formation of a thin fibrous tissue capsule around the tube was observed, indicating good tissue response to the PLGA tube.

Out of ten tubes implanted, nine showed regeneration. One month after implantation, positive reflex responses were observed in 90% of the rats that were implanted with the PLGA microbraided NGC, when the nerve trunks distal to the tubes were pinched in the anaesthetised animals. All these rats had a regenerated cable inside the tubes, which had bridged a 12 mm gap between the nerve stumps. The cables contained numerous fascicles of myelinated as well as unmyelinated axons. Most of the axons in the distal nerve trunks were already myelinated. The thin fibrous tissue capsule around the surface of the tube had new capillaries penetrated and dispersed, indicating good tissue response to the PLGA tube. Immunostaining with an antibody against the NF68 protein confirmed axon distribution through the whole regenerated cable. The PLGA microbraided NGC was biocompatible and showed no inflammatory response which is clinically desirable in minimizing adhesions of an implanted tube to surrounding tissues.

Transverse sections through the mid-point of the 12 mm gaps of the regenerated nerve samples were analysed to determine the total number of fibers, fiber diameter, and fiber density. The results are presented in Table 1 below.

etration of broken tubes into the fibrin matrix cable would hinder the process of nerve regeneration. The PLGA conduits showed no tube breakage after implantation and so, not surprisingly, there were no pieces of broken tube found in the cross-section of the regenerated nerve.

From the foregoing study, it will be apparent that the PLGA tubes may be used with a high degree of success even where they have no additional exterior, or interior, coating or layer. Furthermore, this level of success was achieved without filling the tube with any nerve growth promoting factors. The tubes in the study avoided tissue infiltration into the tube lumen and did not have axons sprouting out of the tube.

In summary, the PLGA microbraided NGC showed good performance in promoting axonal regeneration, had no inflammatory response, and no swelling. It is biodegradable and degrades from the implantation site after serving its purpose. The tubular structure did not collapse and had the necessary strength to withstand the muscular forces surrounding the tube. The microbraided tube had the required permeability to allow for the passage of nutrients from the external environment into the tube lumen to promote nerve regeneration and at the same time provided the necessary barrier to infiltration of unwanted tissues. Being made of fibers alone, the tube was easy to suture on to the nerve stumps which will be advantageous for clinical applications. Experiments on the right sciatic nerve in rats in the present study showed 90% success rate.

It will be appreciated that the described tubes of this invention have application beyond nerve re-generation. More particularly, the tubes may be bound together and used as tubular scaffolds for a number of diverse purposes. For example, these tubular scaffolds could seed hepatocytes. This structure may therefore function as a bioreactor in a bio-artificial liver assist. Additionally, the tubular scaffolds may be used for vascular grafts, that is, to seed endothelial cells and smooth muscle cells.

Other features and advantages of the invention will be apparent to those skilled in the art and, therefore, the invention is defined in the claims.

What is claimed is:

1. A method of medical treatment comprising:
    implanting a flexible, porous, seamless, biodegradable, biocompatible, fibrous, tube braided from ten strands, wherein each of said strands is a bundle of six fibers,

TABLE 1

Morphometric analysis of the regenerated nerves at the midpoint of PLGA tubes

|  | Type | Number of months implanted | Fiber Diameter | Fiber Density | Area of Cable | Population | No. of Samples |
|---|---|---|---|---|---|---|---|
| Mean ± SD | PLGA tube | 1 | 3.928 ± 1.223 | 19454 ± 9172 | 0.588 ± 0.28 | 11439.87 ± 2568 | 10 |
| Mean ± SD | Control |  | 7.41 ± 0.448 | 15012 ± 3256 | 0.53 ± 0.077 | 7991 ± 2438 | 7 |

As will be apparent from Table 1, compared with the normal control nerves on the other side of the rats, the regenerated nerve in the PLGA tubes had smaller fiber diameter, but much higher fiber density due to branching of the axons during regeneration. The fiber population was also significantly higher in the PLGA tube compared to the control.

Figure 3:
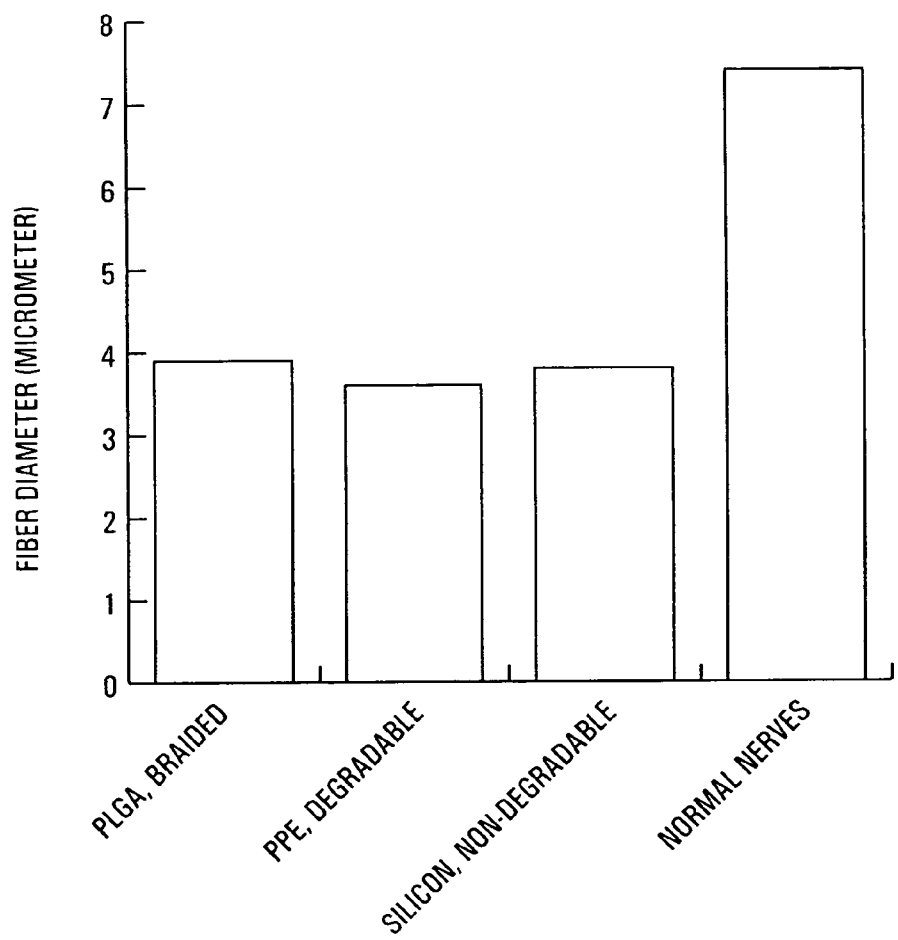
FIG. 3 is a chart of nerve fiber diameter resulting from the use of various NGCs one month after implantation.

FIG. 3 graphically presents some of the data of Table 1 (namely fiber diameter) and adds previously reported experimental results from the published literature for non-fibrous PPE and silicon NGCs. The superior performance of the PLGA tube is noted, with respect to axon diameter. Peneach of said fibers having a diameter of about twenty microns and being one of a poly(L-lactide-co-glycolide) fiber and a chitosan fiber.

2. The method of claim 1 wherein each of said strands makes an interior angle of about forty-five degrees with a central axis of the tube.

3. The method of claim 2 wherein each fiber comprises one or more monofilaments.

4. The method of claim 1 wherein said tube is free of any exterior or interior coating.

5. The method of claim 4 wherein said tube is free of any nerve growth promoting factors.

6. The method of claim 4 wherein a lumen of said tube is free of any nerve growth promoting factors, cells, or fibers.

7. The method of claim 1 wherein a lumen of said tube is filled with a biocompatible medium.

8. The method of claim 7 wherein said biocompatible medium is saline.

9. A medical device, comprising:
a flexible, porous, seamless, biodegradable, biocompatible, fibrous, tube braided from ten strands, wherein each of said strands is a bundle of six fibers, each of said fibers having a diameter of about twenty microns and being one of a poly(L-lactide-co-glycolide) fiber and a chitosan fiber.

10. The device of claim 9 wherein said tube is filled with a biocompatible medium.

11. The device of claim 10 wherein said biocompatible medium is saline.

12. The device of claim 9 wherein each of said strands makes an interior angle of about forty-five degrees with a central axis of the tube.

13. The device of claim 12 wherein each fiber comprises one or more monofilaments.

14. The device of claim 9 wherein said tube is free of any exterior or interior coating.

15. The device of claim 14 wherein said tube is free of any nerve growth promoting factors.

16. The device of claim 14 wherein a lumen of said tube is free of any nerve growth promoting factors, cells, or fibers.

17. A medical device, comprising:
a flexible, porous, seamless, biodegradable, biocompatible, fibrous, tube braided from ten strands, wherein each of said strands is a bundle of six fibers, each of said fibers having a diameter of about twenty microns and being one of a poly(L-lactide-co-glycolide) fiber and a chitosan fiber, said tube being free of any exterior coating.

18. The method of claim 17 wherein each fiber comprises one or more monofilaments.

* * * * *

UNITED STATES PATENT AND TRADEMARK OFFICE
CERTIFICATE OF CORRECTION

| | | |
|---|---|---|
| PATENT NO. | : 7,135,040 B2 | Page 1 of 1 |
| APPLICATION NO. | : 10/328930 | |
| DATED | : November 14, 2006 | |
| INVENTOR(S) | : Wang et al. | |

It is certified that error appears in the above-identified patent and that said Letters Patent is hereby corrected as shown below:

Title page, item (73) Assignee: should read --Assignees:-- and
after the name of the first Assignee, "Agency for Science, Technology and Research, Singapore (SG)." the name of the co-Assignee should be added as follows:
--National University of Singapore, Singapore (SG)--.

Signed and Sealed this

Twelfth Day of August, 2008

JON W. DUDAS
*Director of the United States Patent and Trademark Office*